(12) United States Patent
Oprins

(10) Patent No.: US 9,856,424 B2
(45) Date of Patent: Jan. 2, 2018

(54) INTEGRATED HYDROCRACKING PROCESS

(71) Applicants: SAUDI BASIC INDUSTRIES CORPORATION, Riyadh (SA); SABIC GLOBAL TECHNOLOGIES B.V., Bergen op Zoom (NL)

(72) Inventor: Arno Johannes Maria Oprins, Geleen (NL)

(73) Assignees: Saudi Basic Industries Corporation, Riyadh (SA); Sabic Global Technologies B.V., Bergen op Zoom (NL)

( * ) Notice: Subject to any disclaimer, the term of this patent is extended or adjusted under 35 U.S.C. 154(b) by 0 days.

(21) Appl. No.: 15/121,069

(22) PCT Filed: Dec. 23, 2014

(86) PCT No.: PCT/EP2014/079238
§ 371 (c)(1),
(2) Date: Aug. 24, 2016

(87) PCT Pub. No.: WO2015/128045
PCT Pub. Date: Sep. 3, 2015

(65) Prior Publication Data
US 2016/0362616 A1 Dec. 15, 2016

(30) Foreign Application Priority Data

Feb. 25, 2014 (EP) .................................. 14156636

(51) Int. Cl.
*C10G 69/02* (2006.01)
*C10G 47/26* (2006.01)
(Continued)

(52) U.S. Cl.
CPC ................ *C10G 69/02* (2013.01); *C07C 4/04* (2013.01); *C07C 5/327* (2013.01); *C10G 9/36* (2013.01);
(Continued)

(58) Field of Classification Search
CPC .......... C10G 69/00; C10G 9/00; C10G 69/06; C10G 9/36; C10G 9/005; C10G 2400/22;
(Continued)

(56) References Cited

U.S. PATENT DOCUMENTS 3,839,484 A 10/1974 Zimmerman, Jr. et al.
3,842,138 A 10/1974 Chahvekilian et al.
(Continued)

FOREIGN PATENT DOCUMENTS

CN 101268170 9/2008
EP 0192059 A1 8/1986
GB 2162082 A 1/1986

OTHER PUBLICATIONS

International Search Report for PCT/EP2014/079238 dated Feb. 13, 2015 (3 pages).
(Continued)

*Primary Examiner* — Randy Boyer
*Assistant Examiner* — Juan Valencia
(74) *Attorney, Agent, or Firm* — Norton Rose Fulbright US LLP

(57) ABSTRACT

The present invention relates to an integrated hydrocracking process for production of olefinic and aromatic petro-chemicals from crude oil. An object of the present invention is to provide an integrated hydrocracking process for production of olefinic and aromatic petrochemicals from a hydrocarbon feedstock comprising crude oil wherein the portion of the crude oil converted to LPG is increased significantly.

20 Claims, 1 Drawing Sheet

(51) Int. Cl.
  *C10G 49/22*   (2006.01)
  *C10G 65/10*   (2006.01)
  *C10G 69/06*   (2006.01)
  *C10G 9/36*    (2006.01)
  *C10G 69/10*   (2006.01)
  *C07C 4/04*    (2006.01)
  *C07C 5/327*   (2006.01)

(52) U.S. Cl.
  CPC ............. *C10G 47/26* (2013.01); *C10G 49/22* (2013.01); *C10G 65/10* (2013.01); *C10G 69/06* (2013.01); *C10G 69/10* (2013.01); C10G 2400/20 (2013.01); C10G 2400/22 (2013.01); C10G 2400/30 (2013.01)

(58) Field of Classification Search
  CPC ............ C10G 2400/20; C10G 2400/30; C10B 57/045; Y02P 20/132
  See application file for complete search history.

(56) References Cited

U.S. PATENT DOCUMENTS

| | | | |
|---|---|---|---|
| 4,137,147 A | 1/1979 | Franck et al. | |
| 4,827,072 A | 5/1989 | Imai et al. | |
| 4,926,005 A | 5/1990 | Olbrich et al. | |
| 7,622,623 B2 | 11/2009 | Fridman et al. | |
| 2006/0287561 A1 | 12/2006 | Choi et al. | |
| 2013/0248417 A1 | 9/2013 | Sayed et al. | 208/57 |
| 2013/0248418 A1* | 9/2013 | Sayed | C10G 47/26 208/57 |

OTHER PUBLICATIONS

Office Action issued in Chinese Application No. 201480076217.9, dated Aug. 2, 2017.

* cited by examiner

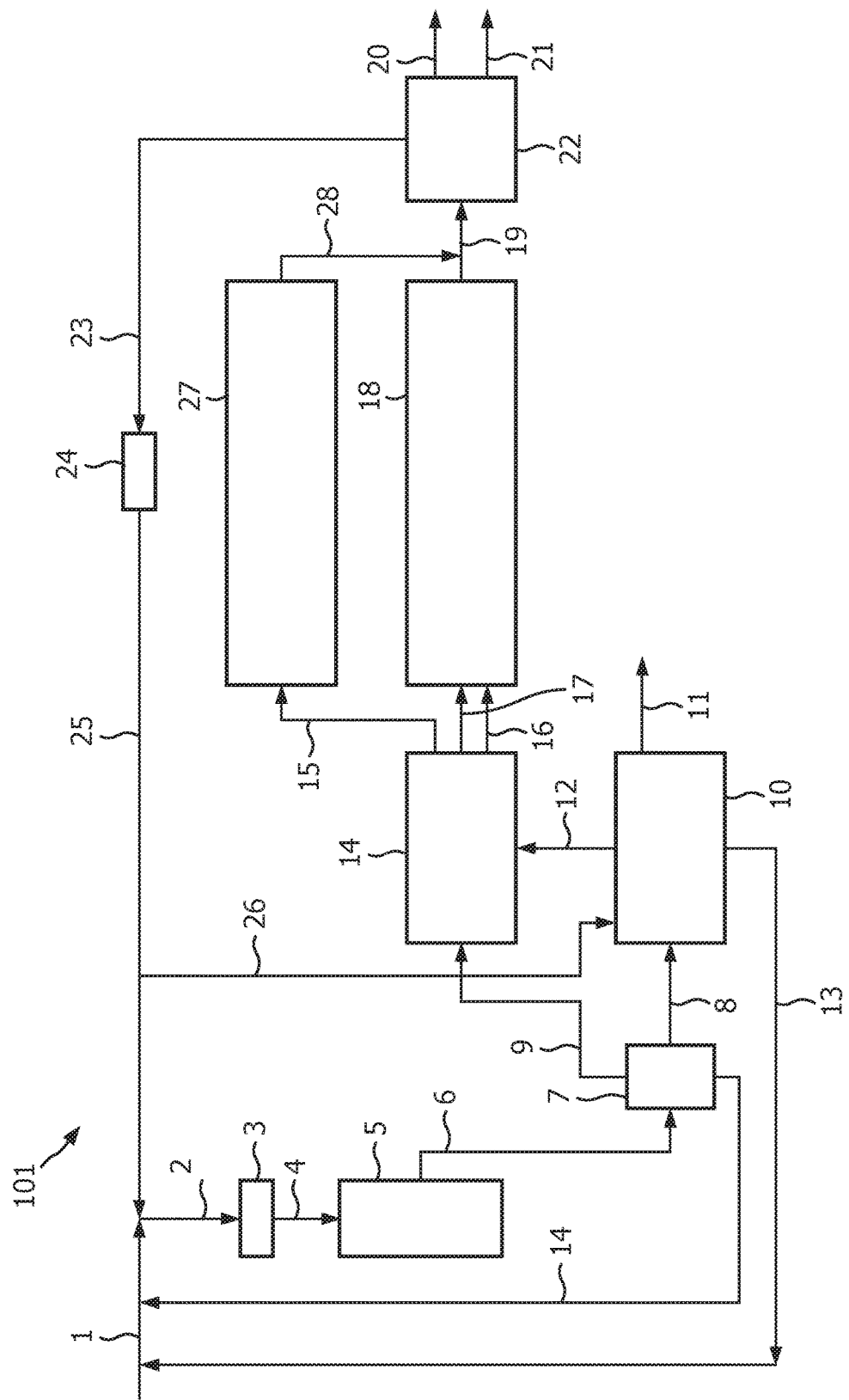

INTEGRATED HYDROCRACKING PROCESS

TECHNICAL FIELD AND BACKGROUND OF THE INVENTION

The present invention relates to an integrated hydrocracking process for production of olefinic and aromatic petrochemicals from a hydrocarbon feedstock comprising crude oil.

Such a process is known from US Patent Application No. 2013/248418. This US Patent Application No. 2013/248418 discloses an integrated slurry hydroprocessing and steam pyrolysis process for the production of olefins and aromatic petrochemicals from a crude oil feedstock. Crude oil, a steam pyrolysis residual liquid fraction and slurry residue are combined and treated in a hydroprocessing zone in the presence of hydrogen under conditions effective to produce an effluent having an increased hydrogen content. The effluent is thermally cracked with steam under conditions effective to produce a mixed product stream and steam pyrolysis residual liquid fraction. The mixed product stream is separated and olefins and aromatics are recovered and hydrogen is purified and recycled. In the process according to US Patent Application No. 2013/248418 the crude oil is hydrocracked to produce a liquid hydrocarbon feed for subsequent processing by means of steam cracking. Steam cracking of heavy liquid feeds results in relatively poor cracker product slate including a relatively small amount of high value chemicals.

U.S. Pat. No. 4,137,147 relates to a process for manufacturing ethylene and propylene from a charge having a distillation point lower than about 360 DEG C. and containing at least normal and iso-paraffins having at least 4 carbon atoms per molecule, wherein: said charge is subjected to a hydrogenolysis reaction in a hydrogenolysis zone, in the presence of a catalyst, (b) the effluents from the hydrogenolysis reaction are fed to a separation zone from which are discharged (i) from the top, methane and possibly hydrogen, (ii) a fraction consisting essentially of hydrocarbons with 2 and 3 carbon atoms per molecule, and (iii) from the bottom, a fraction consisting essentially of hydrocarbons with at least 4 carbon atoms per molecule, (c) only said fraction consisting essentially of hydrocarbons with 2 and 3 carbon atoms per molecule is fed to a steam-cracking zone, in the presence of steam, to transform at least a portion of the hydrocarbons with 2 and 3 carbon atoms per molecule to mono olefinic hydrocarbons; said fraction consisting essentially of hydrocarbons with at least 4 carbon atoms per molecule, obtained from the bottom of said separation zone, is supplied to a second hydrogenolysis zone where it is treated in the presence of a catalyst, the effluent from the second hydrogenolysis zone is supplied to a separation zone to discharge, on the one hand, hydrocarbons with at least 4 carbon atoms per molecule which are recycled at least partly to the said second hydrogenolysis zone, and, on the other hand, a fraction consisting essentially of a mixture of hydrogen, methane and saturated hydrocarbons with 2 and 3 carbon atoms per molecule; a hydrogen stream and a methane stream are separated from said mixture and there is fed to said steam-cracking zone the hydrocarbons of said mixture with 2 and 3 carbon atoms, together with said fraction consisting essentially of hydrocarbons with 2 and 3 carbon atoms per molecule as recovered from said separation zone following the first hydrogenolysis zone. At the outlet of the steam-cracking zone are thus obtained, in addition to a stream of methane and hydrogen and a stream of paraffinic hydrocarbons with 2 and 3 carbon atoms per molecule, olefins with 2 and 3 carbon atoms per molecule and products with at least 4 carbon atoms per molecule.

U.S. Pat. No. 3,842,138 relates to process for thermally cracking a hydrocarbon feedstock to convert it into lower molecular weight products containing large proportions of olefins comprising conducting said process in a heated reactor under superatmospheric pressures, ranging from about 10 bars to about 70 bars read at the reactor outlet, in the presence of hydrogen, at reactor outlet temperatures higher than about 625 C to about 1100 C and with residence times within the reaction section shorter than about 0.5 second down to about 0.005 second. Under the operating conditions the molar ratios of ethylene to ethane and of propylene to propane vary between 0.3 and 2 for the first and between 1 and 8 for the second. In thermal hydrocracking, the temperatures are substantially higher than in the catalytic processes, and under such pyrolytic conditions, the conversion of the charge into gaseous products is higher and may be almost complete, at least as regards the paraffinic hydrocarbons. As for aromatics, due to the more stable structure of the nuclei, only the side chains are affected and are subjected to a more or less intense dealkylation according, to the severity of the operating conditions.

US patent application No. 2006/287561 relates to a process for increasing the production of C2-C4 light olefin hydrocarbons by integrating a process for producing an aromatic hydrocarbon mixture and liquefied petroleum gas (LPG) from a hydrocarbon mixture and a process for producing a hydrocarbon feedstock which is capable of being used as a feedstock in the former process.

U.S. Pat. No. 3,839,484 relates to a process for the preparation of unsaturated hydrocarbons by pyrolysis of naphthas boiling in the range of about 80 to 450 F in a pyrolysis furnace, comprising hydrocracking said naphthas to form a mixture of paraffins and iso paraffins and pyrolyzing the resulting mixture of paraffins and isoparaffins in a pyrolysis furnace An aspect of such an integrated process is that significant amounts of heavier steam cracking components are recycled over the steam cracker ultimately resulting in increased equipment size and energy demand.

Another aspect is that steam cracking of liquid feeds (and LPG with the exception of ethane) furthermore results in significant amounts of methane being produced to be used as fuel in the steam cracking furnaces. This means that some of the more valuable crude oil is therefore downgraded to methane fuel value. In addition to the carbon atoms representing this efficiency loss there is also a lot of hydrogen lost via this methane as well. As a result more hydrogen than necessary needs to be added to the crude oil making the overall hydrogen balances less favorable.

Another aspect of the integrated process is that any LPG made in the hydrocracking processing steps is sent to the compressor and subsequent steam cracker separation section first. The effect thereof is an increase in the sizing and the energy spend in these downstream separations as the desired steam cracking products are diluted first with this LPG (i.e. adding ethane to the ethylene and propane to propylene product to be separated again).

BRIEF SUMMARY OF THE INVENTION

An object of the present invention is to provide an integrated hydrocracking process for production of olefinic and aromatic petrochemicals from a hydrocarbon feedstock comprising crude oil wherein the aforementioned problems have been overcome.

Another object of the present invention is to provide an integrated hydrocracking process for production of olefinic and aromatic petrochemicals from a hydrocarbon feedstock comprising crude oil wherein the portion of the crude oil converted to LPG is increased significantly.

Another object of the present invention is to provide an integrated hydrocracking process for production of olefinic and aromatic petrochemicals from a hydrocarbon feedstock comprising crude oil wherein efficiency and selectivity of the hydrocracking step is by controlled by the severity.

BRIEF DESCRIPTION OF THE DRAWINGS

FIG. 1 depicts a process flow diagram including an integrated hydrocracking process and steam pyrolysis process.

DETAILED DESCRIPTION OF THE INVENTION

The present invention relates thus to an integrated hydrocracking process for production of olefinic and aromatic petrochemicals from a hydrocarbon feedstock comprising crude oil, the process comprising:

treating the feedstock comprising crude oil and a residual liquid stream in a first hydrocracking zone in the presence of hydrogen under conditions effective to produce a first effluent having an increased hydrogen content;

separating the first effluent into a LPG comprising stream and a liquid phase stream;

separating said LPG comprising stream into one or more streams chosen from the group of a stream comprising hydrogen, a stream comprising methane, a stream comprising ethane, a stream comprising butanes, a stream comprising propane, a stream comprising C1-minus, a stream comprising C3-minus, a stream comprising C1-C2, a stream comprising C3-C4, a stream comprising C2-C3, a stream comprising C1-C3, a stream comprising C1-C4, a stream comprising C2-C4, a stream comprising C2-minus, a stream comprising C4-minus;

further processing one or more of the streams thus obtained in a steam cracker unit and at least one unit chosen from the group of a butanes dehydrogenation unit, a propane dehydrogenation unit, a combined propane-butanes dehydrogenation unit, or a combination of units thereof to produce a mixed product stream;

feeding the mixed product stream(s) from said steam cracker unit and at least one unit, chosen from the group of said butanes dehydrogenation unit, said propane dehydrogenation unit, said combined propane-butanes dehydrogenation unit, or a combination of units thereof to a second separation section;

separating the mixed product stream(s).

According to the present invention the LPG comprising stream is separated into one or more streams chosen from the group of a stream comprising hydrogen, a stream comprising methane, a stream comprising ethane, a stream comprising butanes, a stream comprising propane, a stream comprising C1-minus, a stream comprising C3-minus, a stream comprising C1-C2, a stream comprising C3-C4, a stream comprising C2-C3, a stream comprising C1-C3, a stream comprising C1-C4, a stream comprising C2-C4, a stream comprising C2-minus, a stream comprising C4-minus using any appropriate separation technology.

A stream comprising ethane, and/or a stream comprising C1-C2 and/or a stream comprising C2-minus is preferably fed to a gas steam cracking unit. This means that no heavier steam cracking components are recycled over the steam cracker ultimately resulting decreased equipment size and energy demand. Alternative separation scheme's resulting in a combined propane/butanes stream, possibly also diluted with methane and/or ethane or a propane stream possibly diluted with methane and/or ethane can be used. In addition, the propane and butane comprising streams are preferably fed to dehydrogenation units. This processing route results in much higher carbon efficiency and also produces the amounts of hydrogen needed for the high conversion hydrocracking all the way to LPG.

Please note that streams mentioned here with the term "a stream" refer to the stream generated within the present process, i.e. these streams are not from "the outside".

The present method thus focuses on the optimization of the production of LPG comprising streams, which LPG comprising streams are identified as highly useful feedstocks for steam pyrolysis processes and/or dehydrogenation processes for the production of olefinic and aromatic petrochemicals.

Thus the present method comprises the combination of a steam cracker unit and at least one unit chosen from the group of a butanes dehydrogenation unit, a propane dehydrogenation unit, a combined propane-butanes dehydrogenation unit, or a combination of units thereof to produce a mixed product stream. This combination of units provides a high yield of the desired products, namely olefinic and aromatic petrochemicals, wherein the portion of the crude oil converted to LPG is increased significantly.

According to a preferred embodiment the LPG comprising stream is separated into one or more streams, wherein the stream comprising hydrogen is preferably used as a hydrogen source for hydrocracking purpose, the stream comprising methane is preferably used as a fuel source, the stream comprising ethane is preferably used as a feed for the steam cracking unit, the stream comprising propane is preferably used as a feed for a propane dehydrogenation unit, a stream comprising butanes is preferably used as a feed for a butane dehydrogenation unit, a stream comprising C1-minus is preferably used as a fuel source and/or as a hydrogen source, a stream comprising C3-minus is preferably used as a feed for a propane dehydrogenation unit but, according to another embodiment, also as a feed for the steam cracking unit, a stream comprising C2-C3 is preferably used as a feed for a propane dehydrogenation unit, but, according to another embodiment, also as a feed for the steam cracking unit, a stream comprising C1-C3 is preferably used as a feed for a propane dehydrogenation unit, but, according to another embodiment, also as a feed for the steam cracking unit, a stream comprising C1-C4 butanes is preferably used as a feed for a butane dehydrogenation unit, a stream comprising C2-C4 butanes is preferably used as a feed for a butane dehydrogenation unit, a stream comprising C2-minus is preferably used as a feed for the steam cracking unit, a stream comprising C3-C4 is preferably used as a feed for a propane or butane dehydrogenation unit, or a combined propane and butane dehydrogenation unit, a stream comprising C4-minus is preferably used as a feed for a butane dehydrogenation unit.

As used herein, the term "C# hydrocarbons" or "C#", wherein "#" is a positive integer, is meant to describe all hydrocarbons having # carbon atoms. Moreover, the term "C#+ hydrocarbons" or "C#+" is meant to describe all hydrocarbon molecules having # or more carbon atoms. Accordingly, the term "C5+ hydrocarbons" or "C5+" is meant to describe a mixture of hydrocarbons having 5 or more carbon atoms. The term "C5+ alkanes" accordingly relates to alkanes having 5 or more carbon atoms. Accordingly, the term "C# minus hydrocarbons" or "C# minus" is meant to describe a mixture of hydrocarbons having # or less carbon atoms and including hydrogen. For example, the term "C2–" or "C2 minus" relates to a mixture of ethane, ethylene, acetylene, methane and hydrogen. Finally, the term "C4 mix" is meant to describe a mixture of butanes, butenes and butadiene, i.e. n-butane, i-butane, 1-butene, cis- and trans-2-butene, i-butene and butadiene. For example, the term C1-C3 means a mixture comprising C1, C2 and C3.

The term "olefin" is used herein having its well-established meaning. Accordingly, olefin relates to an unsaturated hydrocarbon compound containing at least one carbon-carbon double bond. Preferably, the term "olefins" relates to a mixture comprising two or more of ethylene, propylene, butadiene, butylene-1, isobutylene, isoprene and cyclopentadiene.

The term "LPG" as used herein refers to the well-established acronym for the term "liquefied petroleum gas". LPG generally consists of a blend of C3-C4 hydrocarbons i.e. a mixture of C3 and C4 hydrocarbons.

The one of the petrochemical products produced in the process of the present invention is BTX. The term "BTX" as used herein relates to a mixture of benzene, toluene and xylenes. Preferably, the product produced in the process of the present invention comprises further useful aromatic hydrocarbons such as ethyl benzene. Accordingly, the present invention preferably provides a process for producing a mixture of benzene, toluene xylenes and ethyl benzene ("BTXE"). The product as produced may be a physical mixture of the different aromatic hydrocarbons or may be directly subjected to further separation, e.g. by distillation, to provide different purified product streams. Such purified product stream may include a benzene product stream, a toluene product stream, a xylene product stream and/or an ethyl benzene product stream.

According to the present method a small amount of methane is produced and the methane can be used as fuel for the steam cracking and dehydrogenation furnaces. Any heavier material can be recycled to the different stages of the described process.

The present process further comprises feeding at least one stream chosen from the group of a stream comprising propane, a stream comprising C3-C4, a stream comprising C3-minus, a stream comprising butanes, a stream comprising C4-minus, a stream comprising C2-C3, a stream comprising C1-C3, a stream comprising C1-C4 and a stream comprising C2-C4 to at least one dehydrogenation unit chosen from the group of a butanes dehydrogenation unit, a propane dehydrogenation unit, a combined propane-butanes dehydrogenation unit, or a combination of units thereof.

The present process further comprises recovering olefins and aromatics from the separated mixed product stream.

According to a preferred embodiment the process further comprises:

treating said liquid phase stream in a second hydrocracking zone in the presence of hydrogen under conditions effective to produce a second effluent having an increased hydrogen content;

recovering from the second effluent from said second hydrocracking zone a BTXE comprising stream, a LPG comprising stream and the residual liquid stream. One of the advantages of a second hydrocracking zone is that it gives more control over the efficiency and selectivity of the hydrocracking steps by controlling the severity.

In addition it is preferred to combine the LPG comprising stream originating from said first hydrocracking zone with the LPG comprising stream originating from said second hydrocracking zone. Such a combined LPG comprising stream can be further separated into individual streams as discussed above and processed accordingly.

According to a preferred embodiment the process further comprises recycling said residual liquid stream from said second hydrocracking zone and/or said liquid phase stream to inlet of the first hydrocracking zone.

As discussed before, it is preferred to recover methane from the separated mixed product stream(s) and to recycle said methane to the steam cracker to be used as fuel for burners and/or heaters.

According to a preferred embodiment the process further comprises recovering and possibly purifying hydrogen from the separated mixed product stream(s) and recycling it to the inlet of the first and/or second hydrocracking zone.

According to another preferred embodiment the process further comprises recovering pyrolysis fuel oil from the separated mixed product stream(s) and recycling said pyrolysis fuel oil to the inlet of said first and/or second hydrocracking.

A very common process for the conversion of alkanes to olefins involves "steam cracking" As used herein, the term "steam cracking" relates to a petrochemical process in which saturated hydrocarbons are broken down into smaller, often unsaturated, hydrocarbons such as ethylene and propylene. In steam cracking gaseous hydrocarbon feeds like ethane, propane and butanes, or mixtures thereof, (gas cracking) or liquid hydrocarbon feeds like naphtha or gas oil (liquid cracking) is diluted with steam and briefly heated in a furnace without the presence of oxygen. Typically, the reaction temperature is very high, at around 850° C., but the reaction is only allowed to take place very briefly, usually with residence times of 50-500 milliseconds. Preferably, the hydrocarbon compounds ethane, propane and butanes are separately cracked in accordingly specialized furnaces to ensure cracking at optimal conditions. After the cracking temperature has been reached, the gas is quickly quenched to stop the reaction in a transfer line heat exchanger or inside a quenching header using quench oil. Steam cracking results in the slow deposition of coke, a form of carbon, on the reactor walls. Decoking requires the furnace to be isolated from the process and then a flow of steam or a steam/air mixture is passed through the furnace coils. This converts the hard solid carbon layer to carbon monoxide and carbon dioxide. Once this reaction is complete, the furnace is returned to service. The products produced by steam cracking depend on the composition of the feed, the hydrocarbon to steam ratio and on the cracking temperature and furnace residence time. Light hydrocarbon feeds such as ethane, propane, butanes or light naphtha give product streams rich in the lighter polymer grade olefins, including ethylene, propylene, and butadiene. Heavier hydrocarbon (full range and heavy naphtha and gas oil fractions) also give products rich in aromatic hydrocarbons.

To separate the different hydrocarbon compounds produced by steam cracking the cracked gas is subjected to fractionation unit. Such fractionation units are well known in the art and may comprise a so-called gasoline fractionator where the heavy-distillate ("carbon black oil") and the middle-distillate ("cracked distillate") are separated from the light-distillate and the gases. In the subsequent quench tower, most of the light-distillate produced by steam cracking ("pyrolysis gasoline" or "pygas") may be separated from the gases by condensing the light-distillate. Subsequently, the gases may be subjected to multiple compression stages wherein the remainder of the light distillate may be separated from the gases between the compression stages. Also acid gases (CO2 and H2S) may be removed between compression stages. In a following step, the gases produced by pyrolysis may be partially condensed over stages of a cascade refrigeration system to about where only the hydrogen remains in the gaseous phase. The different hydrocarbon compounds may subsequently be separated by simple distillation, wherein the ethylene, propylene and C4 olefins are the most important high-value chemicals produced by steam cracking. The methane produced by steam cracking is generally used as fuel gas, the hydrogen may be separated and recycled to processes that consume hydrogen, such as hydrocracking processes. The acetylene produced by steam cracking preferably is selectively hydrogenated to ethylene. The alkanes comprised in the cracked gas may be recycled to the process for converting alkanes to olefins.

The term "propane dehydrogenation unit" as used herein relates to a petrochemical process unit wherein a propane feedstream is converted into a product comprising propylene and hydrogen. Accordingly, the term "butane dehydrogenation unit" relates to a process unit for converting a butane feedstream into C4 olefins. Together, processes for the dehydrogenation of lower alkanes such as propane and butanes are described as lower alkane dehydrogenation process. Processes for the dehydrogenation of lower alkanes are well-known in the art and include oxidative hydrogenation processes and non-oxidative dehydrogenation processes. In an oxidative dehydrogenation process, the process heat is provided by partial oxidation of the lower alkane(s) in the feed. In a non-oxidative dehydrogenation process, which is preferred in the context of the present invention, the process heat for the endothermic dehydrogenation reaction is provided by external heat sources such as hot flue gases obtained by burning of fuel gas or steam. For instance, the UOP Oleflex process allows for the dehydrogenation of propane to form propylene and of (iso)butane to form (iso)butylene (or mixtures thereof) in the presence of a catalyst containing platinum supported on alumina in a moving bed reactor; see e.g. U.S. Pat. No. 4,827,072. The Uhde STAR process allows for the dehydrogenation of propane to form propylene or of butane to form butylene in the presence of a promoted platinum catalyst supported on a zinc-alumina spinel; see e.g. U.S. Pat. No. 4,926,005. The STAR process has been recently improved by applying the principle of oxydehydrogenation. In a secondary adiabatic zone in the reactor part of the hydrogen from the intermediate product is selectively converted with added oxygen to form water. This shifts the thermodynamic equilibrium to higher conversion and achieve higher yield. Also the external heat required for the endothermic dehydrogenation reaction is partly supplied by the exothermic hydrogen conversion. The Lummus Catofin process employs a number of fixed bed reactors operating on a cyclical basis. The catalyst is activated alumina impregnated with 18-20 wt-% chromium; see e.g. EP 0 192 059 A1 and GB 2 162 082 A. The Catofin process is reported to be robust and capable of handling impurities which would poison a platinum catalyst. The products produced by a butane dehydrogenation process depends on the nature of the butane feed and the butane dehydrogenation process used. Also the Catofin process allows for the dehydrogenation of butane to form butylene; see e.g. U.S. Pat. No. 7,622,623.

Other aspects, embodiments, and advantages of the process of the present invention are discussed in detail below. Moreover, it is to be understood that both the foregoing information and the following detailed description are merely illustrative examples of various aspects and embodiments, and are intended to provide an overview or framework for understanding the nature and character of the claimed features and embodiments. The accompanying drawing is illustrative and is provided to further understanding of the various aspects and embodiments of the process of the invention.

A process flow diagram including integrated hydrocracking process and steam pyrolysis process is shown in FIG. 1. The integrated system 101 includes a hydrocracking zone, a steam pyrolysis zone, a dehydrogenation zone and a product separation zone.

A blending zone 3 is provided that includes one or more inlets for receiving a feed 1, a recycled hydrogen stream 25, a converted residual liquid stream 13 from a second hydrocracking zone 10, a liquid phase stream 14 from separation unit 7. Mixed stream 2 is thus sent to blending zone 3, further including an outlet for discharging a mixed stream 4. Hydrocracking zone 5 includes an inlet for receiving the mixed stream 4 and makeup hydrogen as necessary (not shown). Hydrocracking zone 5 further includes an outlet for discharging a hydrocracked effluent 6. Hydrocracked effluent 6 is sent to separation unit 7 resulting in a LPG comprising stream 9, a liquid phase stream 8 and, possibly, a residual liquid fraction 14. In a preferred embodiment (not shown here) separation unit 7 also provides a hydrogen comprising stream, which stream can be routed to the inlet of hydrocracking zone 5. According to another embodiment (not shown here) effluent 6 is sent to a high pressure separator and the hydrogen thus separated is routed to the inlet of hydrocracking zone 5, as well.

LPG comprising stream 9 is sent to separation unit 14 to be separated into one or more gaseous streams 15, 16, 17 chosen from the group of a stream comprising hydrogen, a stream comprising methane, a stream comprising ethane, a stream comprising butanes, a stream comprising propane, a stream comprising C1-minus, a stream comprising C3-minus, a stream comprising C1-C2, a stream comprising C3-C4, a stream comprising C2-C3, a stream comprising C1-C3, a stream comprising C1-C4, a stream comprising C2-C4, a stream comprising C2-minus, a stream comprising C4-minus. Although the enclosed FIGURE only displays streams 15, 16, 17 coming from separation unit 14 it is however possible that more individual streams are obtained in separation unit 14. For example, stream 15 is a stream comprising C2-minus, stream 17 is a stream comprising propane and stream 16 is a stream comprising butanes. On basis of the composition of stream 15 it is preferred to send this stream 15 to a separate unit 27, i.e. a gas steam cracker unit 27. The effluent 28 from steam cracker unit 27 is sent to separation unit 22. Separation unit 22 may comprise several individual separation units. Although only three individual streams 15, 16, 17 have been shown, the present invention is not restricted to any number of individual streams. Liquid phase stream 8 is processed in a second hydrocracking zone 10 producing a LPG comprising stream 12, a BTXE comprising stream 11 and a residual liquid stream 13. Stream 13 is preferably recycled to the inlet of first hydrocracking zone 5. In a specific embodiment, especially when stream 13 contains a sufficient amount of olefins, stream 13 can be (partly) sent to separation unit 22.

Individual streams 16, 17 are further processed in unit 18, wherein unit 18 is at least one unit chosen from the group of a butanes dehydrogenation unit, a propane dehydrogenation unit a combined propane-butanes dehydrogenation unit, or a combination of units thereof to produce a mixed product stream 19. Unit 18 also comprises a separation section 22 for separating the mixed product streams 19, 28 into individual streams 20, 21. From individual streams 20, 21 olefins and aromatics can be recovered. Although only two individual streams 20, 21 have been shown, the present invention is not restricted to any number of individual streams. Stream 23 is a stream comprising hydrogen. Methane part can be separated in unit 22 and recycled to the steam cracker and/or butanes dehydrogenation unit, propane dehydrogenation unit and combined propane-butanes dehydrogenation unit of unit 18 to be used as fuel for burners and/or heaters. Hydrogen stream 23 is then optionally passed to a hydrogen purification unit 24, such as a pressure swing adsorption (PSA) unit to obtain a hydrogen stream 25 having a purity of 99.9%+, or a membrane separation units to obtain a hydrogen stream 25 with a purity of about 95%, or any other suitable hydrogen purification technology. The purified hydrogen stream 25 is then recycled back to serve as a major portion of the required hydrogen for the hydroprocessing reaction zone 5, or a part 26 thereof is recycled back to serve as a major portion of the required hydrogen for the second hydrocracking zone 10. Liquid phase stream 8 serves as the feed to the second hydrocracking zone 10. Pyrolysis fuel oil can recovered from mixed product stream 19 and recycled to the inlet of said first and/or second hydrocracking zone 5, 10.

Although second hydrocracking zone 10 has been shown here as a single box, in the present description reference number 10 is to be understood as a hydrocracking zone, i.e. a hydrocracking zone comprising one or more units chosen from the group of Feed Hydrocracking (FHC), Gasoline Hydrocracking (GHC), Aromatic Ringopening, Hydrocracking (gas oil) and Resid Hydrocracking (vacuum resid), including separation sections.

The preferred FHC conditions include a temperature of 300-550° C., a pressure of 300-5000 kPa gauge and a Weight Hourly Space Velocity of 0.1-10 h−1. More preferred feed hydrocracking conditions (FHC) include a temperature of 300-450° C., a pressure of 300-5000 kPa gauge and a Weight Hourly Space Velocity of 0.1-10 h−1. Even more preferred FHC conditions optimized to the ring-opening of aromatic hydrocarbons include a temperature of 300-400° C., a pressure of 600-3000 kPa gauge and a Weight Hourly Space Velocity of 0.2-2 h−1. The preferred gasoline hydrocracking conditions (GHC) include a temperature of 300-580° C., more preferably of 400-580° C. and even more preferably of 430-530° C., a pressure of 0.3-5 MPa gauge, more preferably at a pressure of 0.6-3 MPa gauge, particularly preferably at a pressure of 1-2 MPa gauge and most preferably at a pressure of 1.2-1.6 MPa gauge, and a Weight Hourly Space Velocity (WHSV) of 0.1-20 h−1, more preferably at a Weight Hourly Space Velocity of 0.2-15 h−1 and most preferably at a Weight Hourly Space Velocity of 0.4-10 h−1. The aromatic ring opening process (ARO process, see for example U.S. Pat. No. 7,513,988) may comprise aromatic ring saturation at a temperature of 100-500° C., preferably 200-500° C., more preferably 300-500° C., a pressure of 2-10 MPa together with 1-30 wt.-%, preferably 5-30 wt.-% of hydrogen (in relation to the hydrocarbon feedstock) in the presence of an aromatic hydrogenation catalyst and ring cleavage at a temperature of 200-600° C., preferably 300-400° C., a pressure of 1-12 MPa together with 1-20 wt.-% of hydrogen (in relation to the hydrocarbon feedstock) in the presence of a ring cleavage catalyst, wherein said aromatic ring saturation and ring cleavage may be performed in one reactor or in two consecutive reactors. The process conditions used for hydrocracking generally includes a process temperature of 200-600° C., elevated pressures of 0.2-20 MPa, and space velocities between 0.1-20 h−1.

In a preferred embodiment hydrocracking zone 5 is a resid hydrocracker. Resid hydrocracking processes are well known in the art; see e.g. Alfke et al. (2007) Oil Refining, Ullmann's Encyclopedia of Industrial Chemistry and Speight (2005) Petroleum Refinery Processes, Kirk-Othmer Encyclopedia of Chemical Technology. Accordingly, three basic reactor types are employed in commercial hydrocracking which are a fixed bed (trickle bed) reactor type, an ebullated bed reactor type and slurry (entrained flow) reactor type. Fixed bed resid hydrocracking processes are well-established and are capable of processing contaminated streams such as atmospheric residues and vacuum residues to produce light- and middle-distillate which can be further processed to produce olefins and aromatics. The catalysts used in fixed bed resid hydrocracking processes commonly comprise one or more elements selected from the group consisting of Co, Mo and Ni on a refractory support, typically alumina. In case of highly contaminated feeds, the catalyst in fixed bed resid hydrocracking processes may also be replenished to a certain extend (moving bed). The process conditions commonly comprise a temperature of 350-450° C. and a pressure of 2-20 MPa gauge. Ebullated bed resid hydrocracking processes are also well-established and are inter alia characterized in that the catalyst is continuously replaced allowing the processing of highly contaminated feeds. The catalysts used in ebullated bed resid hydrocracking processes commonly comprise one or more elements selected from the group consisting of Co, Mo and Ni on a refractory support, typically alumina. The small particle size of the catalysts employed effectively increases their activity (c.f. similar formulations in forms suitable for fixed bed applications). These two factors allow ebullated hydrocracking processes to achieve significantly higher yields of light products and higher levels of hydrogen addition when compared to fixed bed hydrocracking units. The process conditions commonly comprise a temperature of 350-450° C. and a pressure of 5-25 MPa gauge. Slurry resid hydrocracking processes represent a combination of thermal cracking and catalytic hydrogenation to achieve high yields of distillable products from highly contaminated resid feeds. In the first liquid stage, thermal cracking and hydrocracking reactions occur simultaneously in the fluidized bed at process conditions that include a temperature of 400-500° C. and a pressure of 15-25 MPa gauge. Resid, hydrogen and catalyst are introduced at the bottom of the reactor and a fluidized bed is formed, the height of which depends on flow rate and desired conversion. In these processes catalyst is continuously replaced to achieve consistent conversion levels through an operating cycle. The catalyst may be an unsupported metal sulphide that is generated in situ within the reactor. In practice the additional costs associated with the ebullated bed and slurry phase reactors are only justified when a high conversion of highly contaminated heavy streams such as vacuum gas oils is required. Under these circumstances the limited conversion of very large molecules and the difficulties associated with catalyst deactivation make fixed bed processes relatively unattractive in the process of the present invention. Accordingly, ebullated bed and slurry reactor types are preferred due to their improved yield of light- and middle-distillate when compared to fixed bed hydrocracking. The term "resid upgrading liquid effluent" relates to the product produced by resid upgrading excluding the gaseous products, such as methane and LPG, and the heavy-distillate produced by resid upgrading. The heavy-distillate produced by resid upgrading is preferably recycled to the resid upgrading unit until extinction. However, it may be necessary to purge a relatively small pitch stream. From the viewpoint of carbon efficiency, a resid hydrocracker is preferred over a coking unit as the latter produces considerable amounts of petroleum coke that cannot be upgraded to high value petrochemical products. From the viewpoint of the hydrogen balance of the integrated process, it may be preferred to select a coking unit over a resid hydrocracker as the latter consumes considerable amounts of hydrogen. Also in view of the capital expenditure and/or the operating costs it may be advantageous to select a coking unit over a resid hydrocracker.

The invention claimed is:

1. An integrated hydrocracking process for production of olefinic and aromatic petrochemicals from a hydrocarbon feedstock comprising crude oil, the process comprising:
   treating the hydrocarbon feedstock comprising crude oil and a residual liquid stream in a first hydrocracking zone in the presence of hydrogen under conditions effective to produce a first effluent having an increased hydrogen content;
   separating the first effluent into a liquefied petroleum gas (LPG) comprising stream and a liquid phase stream;
   separating said LPG comprising stream into one or more streams chosen from a stream comprising hydrogen, a stream comprising methane, a stream comprising ethane, a stream comprising butanes, a stream comprising propane, and a stream comprising C4-minus;
   further processing one or more of the streams obtained in a steam cracker unit and at least one unit chosen from-the group of a butanes dehydrogenation unit, a propane dehydrogenation unit, a combined propane-butanes dehydrogenation unit, or a combination of units thereof to produce mixed product stream(s);
   feeding the mixed product stream(s) from said steam cracker unit and said at least one unit, chosen from the group of said butanes dehydrogenation unit, a said propane dehydrogenation unit, said combined propane-butanes dehydrogenation unit, or said combination of units thereof to a second separation section; and
   separating the mixed product stream(s).

2. An integrated hydrocracking process for production of olefinic and aromatic petrochemicals from a hydrocarbon feedstock comprising crude oil, the process comprising:
   treating the hydrocarbon feedstock comprising crude oil and a residual liquid stream in a first hydrocracking zone in the presence of hydrogen under conditions effective to produce a first effluent having an increased hydrogen content;
   separating the first effluent into a liquefied petroleum gas (LPG) comprising stream and a liquid phase stream;
   separating said LPG comprising stream into one or more streams chosen from a stream comprising hydrogen, a stream comprising ethane and a stream comprising C2-minus;
   further processing one or more of the streams obtained in a steam cracker unit and at least one unit chosen from-the group of a butanes dehydrogenation unit, a propane dehydrogenation unit, a combined propane-butanes dehydrogenation unit, or a combination of units thereof to produce at least one mixed product stream;
   feeding the at least one mixed product stream from said steam cracker unit and said at least one unit, chosen from the group of said butanes dehydrogenation unit, a said propane dehydrogenation unit, said combined propane-butanes dehydrogenation unit, or said combination of units thereof to a second separation section;
   separating the at least one mixed product stream; and feeding at least one stream chosen from said stream comprising ethane and said stream comprising C2-minus to said steam cracker unit.

3. The process according to claim 1, further comprising feeding at least one stream chosen from said stream comprising propane and said stream comprising C4-minus to at least one dehydrogenation unit chosen from said butanes dehydrogenation unit, said propane dehydrogenation unit, said combined propane-butanes dehydrogenation unit, or a combination of units thereof.

4. The process according to claim 1, further comprising recovering olefins and aromatics from the separated mixed product stream(s).

5. The process of claim 1, further comprising:
   treating said liquid phase stream in a second hydrocracking zone in the presence of hydrogen under conditions effective to produce a second effluent having an increased hydrogen content;
   recovering from the second effluent from said second hydrocracking zone a mixture of benzene, toluene xylenes and ethyl benzene (BTXE) comprising stream, a LPG comprising stream and said residual liquid stream.

6. The process according to claim 5, further comprising combining the LPG comprising stream originating from said first hydrocracking zone with the LPG comprising stream originating from said second hydrocracking zone.

7. The process according to claim 5, further comprising recycling said residual liquid stream from said second hydrocracking zone and/or said liquid phase stream to inlet of the first hydrocracking zone.

8. The process according to claim 1, further comprising recovering methane from the separated mixed product stream(s) and recycling said methane to the steam cracker to be used as fuel for burners and/or heaters.

9. The process according to claim 5, further comprising recovering and purifying hydrogen from the separated mixed product stream(s) and recycling it to the inlet of the first and/or second hydrocracking zone.

10. The process according to claim 5, further comprising recovering pyrolysis fuel oil from the separated mixed product stream(s) and recycling said pyrolysis fuel oil to the inlet of said first and/or second hydrocracking zone.

11. An integrated hydrocracking process for production of olefinic and aromatic petrochemicals from a hydrocarbon feedstock comprising crude oil, the process comprising:
   treating the hydrocarbon feedstock comprising crude oil and a residual liquid stream in a first hydrocracking zone in the presence of hydrogen under conditions effective to produce a first effluent having an increased hydrogen content;
   separating the first effluent into a liquefied petroleum gas (LPG) comprising stream and a liquid phase stream;
   separating said LPG comprising stream into one or more streams chosen from a stream comprising hydrogen, a stream comprising methane, a stream comprising ethane, a stream comprising butanes, a stream comprising propane, a stream comprising C2-C3,
   further processing one or more of the streams obtained in a steam cracker unit and at least one unit chosen from-the group of a butanes dehydrogenation unit, a propane dehydrogenation unit, a combined propane-butanes dehydrogenation unit, or a combination of units thereof to produce at least one mixed product stream;
   feeding the at least one mixed product stream from said steam cracker unit and said at least one unit, chosen from the group of said butanes dehydrogenation unit, a said propane dehydrogenation unit, said combined propane-butanes dehydrogenation unit, or said combination of units thereof to a second separation section; and separating the at least one mixed product stream.

12. The process according to claim 2, further comprising recovering olefins and aromatics from the separated mixed product stream(s).

13. The process according to claim 11, further comprising recovering olefins and aromatics from the separated at least one mixed product stream.

14. The process according to claim 5, further comprising recovering hydrogen from the separated mixed product stream(s) and recycling it to the inlet of the first and/or second hydrocracking zone.

15. The process according to claim 5, further comprising recovering pyrolysis fuel oil from the separated mixed product stream(s).

16. The process according to claim 5, further comprising recycling said residual liquid stream from said second hydrocracking zone.

17. The process according to claim 5, further comprising recycling said liquid phase stream to inlet of the first hydrocracking zone.

18. The process according to claim 1, further comprising recovering methane from the separated mixed product stream.

19. The process of claim 1, further comprising:
treating said liquid phase stream in a second hydrocracking zone in the presence of hydrogen under conditions effective to produce a second effluent having an increased hydrogen content.

20. The process of claim 5, further comprising recovering from the second effluent from said second hydrocracking zone the LPG comprising stream.

* * * * *